(12) United States Patent
Echizenya et al.

(10) Patent No.: US 10,987,380 B2
(45) Date of Patent: Apr. 27, 2021

(54) HYDROZINCITE CONTAINING ZINC CARBONATE HYDROXIDE HYDRATE AND METHOD OF MAKING

(71) Applicant: JFE MINERAL COMPANY, LTD., Tokyo (JP)

(72) Inventors: Yuko Echizenya, Tokyo (JP); Yoshimi Nakata, Tokyo (JP); Etsurou Udagawa, Tokyo (JP); Osamu Yamamoto, Yamagata (JP)

(73) Assignee: JFE MINERAL COMPANY, LTD., Tokyo (JP)

( * ) Notice: Subject to any disclaimer, the term of this patent is extended or adjusted under 35 U.S.C. 154(b) by 0 days.

(21) Appl. No.: 16/468,227

(22) PCT Filed: Dec. 8, 2017

(86) PCT No.: PCT/JP2017/044225
§ 371 (c)(1),
(2) Date: Jun. 10, 2019

(87) PCT Pub. No.: WO2018/105739
PCT Pub. Date: Jun. 14, 2018

(65) Prior Publication Data
US 2020/0078396 A1    Mar. 12, 2020

(30) Foreign Application Priority Data
Dec. 9, 2016 (JP) .................................. 2016-239801

(51) Int. Cl.
*A61K 33/30* (2006.01)
*A61L 15/18* (2006.01)
(Continued)

(52) U.S. Cl.
CPC .............. *A61K 33/30* (2013.01); *A61L 15/18* (2013.01); *A61L 15/44* (2013.01); *A61P 17/02* (2018.01);
(Continued)

(58) Field of Classification Search
CPC ......... A61K 33/30; A61K 45/06; A61P 17/02; A61L 15/18; A61L 15/44; C01G 9/006;
(Continued)

(56) References Cited

U.S. PATENT DOCUMENTS 7,234,582 B2   6/2007  Umeda
8,119,168 B2   2/2012  Johnson et al.
(Continued)

FOREIGN PATENT DOCUMENTS

CN    1183950 C     1/2005
CN    101663237 A   3/2010
(Continued)

OTHER PUBLICATIONS

Extended European Search Report issued in European Patent Application No. 17879014.3 dated Nov. 20, 2019.
(Continued)

*Primary Examiner* — Carlos A Azpuru
(74) *Attorney, Agent, or Firm* — Nixon & Vanderhye

(57) ABSTRACT

An inorganic composition that is useful as an active ingredient for pharmaceuticals and has excellent stability comprises hydrozincite-containing zinc carbonate hydroxide hydrate produced by drying a precipitate. The precipitate is obtained by adding aqueous zinc nitrate solution, aqueous zinc sulfate solution or aqueous zinc chloride solution and aqueous sodium hydroxide solution dropwise to aqueous sodium hydrogen carbonate solution, a pH of the aqueous sodium hydrogen carbonate solution being maintained within a range of 6.5 to 9 by means of a pH controller. The
(Continued)

hydrozincite-containing zinc carbonate hydroxide hydrate has an amount of dissolved $Zn^{2+}$ ions of not less than 0.1 µg/m² but not more than 7.33 µg/m² and pH of not less than 7.2 and less than 8.3 after a dissolution test using stirring method.

14 Claims, 6 Drawing Sheets

(51) Int. Cl.
    *A61L 15/44*     (2006.01)
    *A61P 17/02*     (2006.01)
    *C01G 9/00*     (2006.01)

(52) U.S. Cl.
    CPC .......... *C01G 9/006* (2013.01); *C01P 2002/72* (2013.01); *C01P 2002/74* (2013.01); *C01P 2006/12* (2013.01); *C01P 2006/80* (2013.01)

(58) Field of Classification Search
    CPC .............. C01P 2002/72; C01P 2002/74; C01P 2006/12; C01P 2006/80
    See application file for complete search history.

(56) References Cited

U.S. PATENT DOCUMENTS

| | | | |
|---|---|---|---|
| 2003/0133991 | A1 | 7/2003 | Monroe et al. |
| 2003/0215522 | A1 | 11/2003 | Johnson et al. |
| 2004/0076662 | A1 | 4/2004 | Riesinger |
| 2004/0076686 | A1 | 4/2004 | Riesinger |
| 2005/0020199 | A1 | 1/2005 | Umeda |
| 2005/0181067 | A1 | 8/2005 | Yokoyama et al. |
| 2008/0063618 | A1 | 3/2008 | Johnson et al. |
| 2008/0138442 | A1 | 6/2008 | Johnson et al. |
| 2010/0108941 | A1 | 5/2010 | Suginobe et al. |
| 2014/0017296 | A1 | 1/2014 | Sidenius et al. |
| 2018/0311277 | A1 | 11/2018 | Udagawa et al. |
| 2018/0318343 | A1 | 11/2018 | Udagawa et al. |

FOREIGN PATENT DOCUMENTS

| | | | |
|---|---|---|---|
| CN | 103479590 | | 1/2014 |
| CN | 103622885 | | 3/2014 |
| CN | 104546629 | | 4/2015 |
| CN | 107635568 | A | 1/2018 |
| JP | 2004-161684 | | 6/2004 |
| JP | 2004-269372 | | 9/2004 |
| JP | 2004-534560 | | 11/2004 |
| JP | 2005-006995 | | 1/2005 |
| JP | 2005-515191 | | 5/2005 |
| JP | 2005-524690 | | 8/2005 |
| JP | 2014-511851 | | 5/2014 |
| JP | 201780075441 | A | 12/2020 |
| WO | 1996/025913 | A1 * | 8/1996 |
| WO | WO1996/025913 | | 8/1996 |
| WO | 2003082229 | A1 * | 10/2003 |
| WO | WO 03/088957 | | 10/2003 |
| WO | WO 2003/082229 | | 10/2003 |
| WO | 2016199907 | A * | 12/2016 |
| WO | WO 2016/199907 | | 12/2016 |

OTHER PUBLICATIONS

International Search Report, PCT/JP2017/044225, dated Jan. 23, 2018.

2009, 2008, pp. 2, 3, ISBN: 978-4-8407-3863-7, 262, 264, (Drugs in Japan Ethical Drugs 2009), non-official translation ("skin disease treatment agents 262, 264, zinc oxide").

Wang, M. M. et al., Mutagenicity of ZnO nanopartices in mammalian cells: Role of physicochemical transformations under the aging process, Nanotoxicology, Feb. 13, 2015, early online: pp. 1-11, ISSN: 1743-5404.

Office Action issued in European Patent Application No. 17 879 014.3 dated Sep. 3, 2020.

Office Action issued in Chinese Patent Application No. 201780075441 dated Dec. 17, 2020 with English translation of the Search Report provided.

\* cited by examiner

FIG. 2
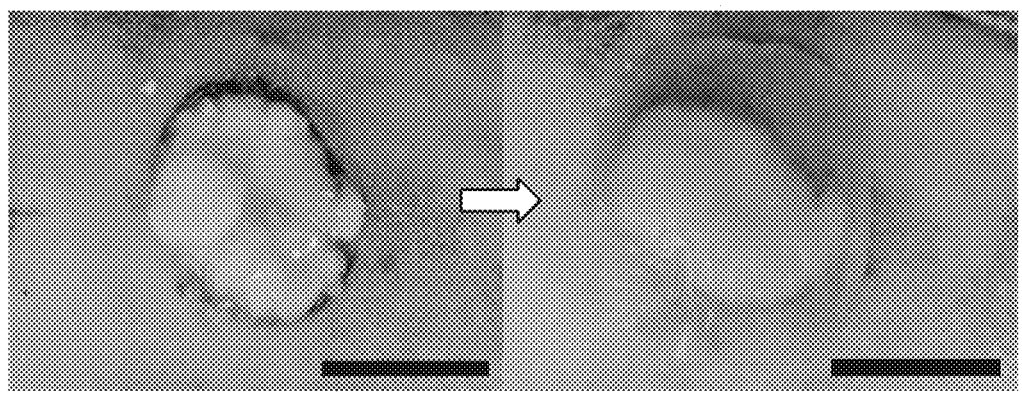
PHOTOGRAPH WHERE POWDER OF PREPARATION EXAMPLE 1 WAS APPLIED TO 10 mm OF FULL THICKNESS SKIN LOSS.
PHOTOGRAPH WHERE POWDER OF PREPARATION EXAMPLE 1 WAS APPLIED AND THEN COATED WITH MEDICAL DUOACTIVE.
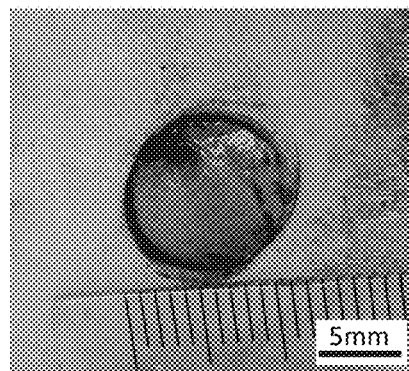
FIG. 3A
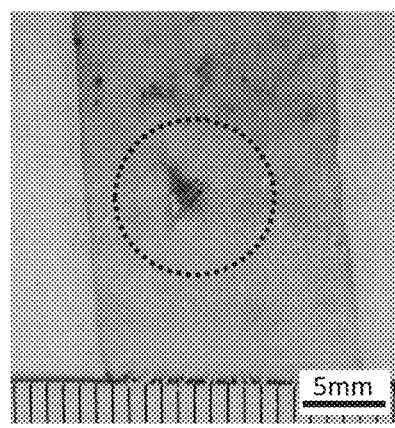
FIG. 3B
FIG. 4
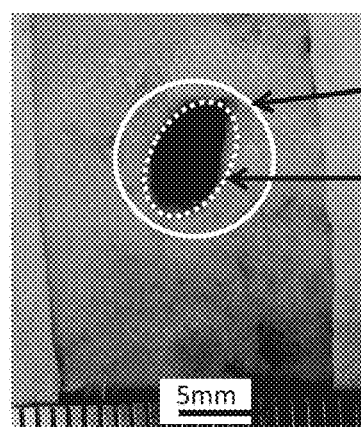
INITIAL WOUND SITE ($W_0$)
UNHEALED SITE ($W_t$)

PHARMACEUTICAL EXAMPLE 1

NORMAL SKIN

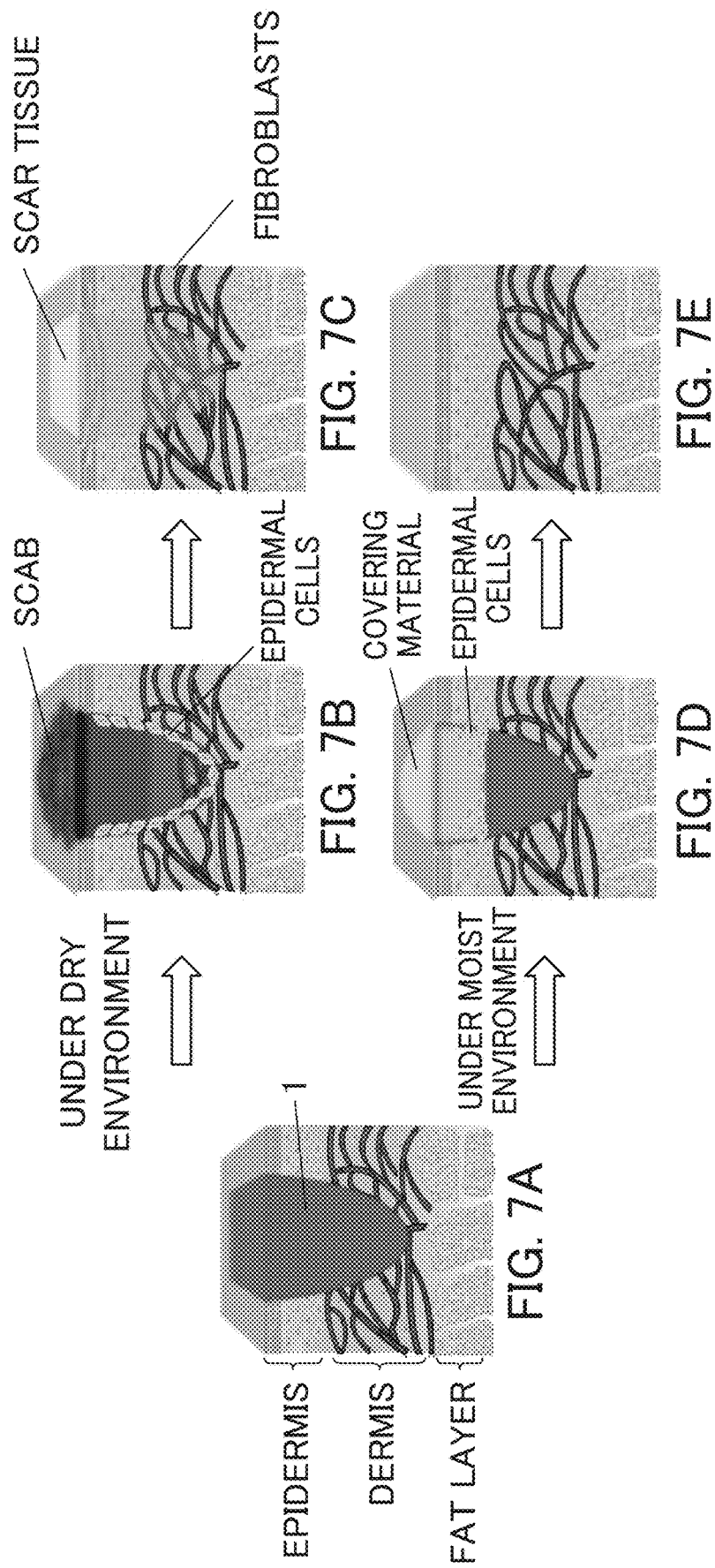

US 10,987,380 B2

HYDROZINCITE CONTAINING ZINC CARBONATE HYDROXIDE HYDRATE AND METHOD OF MAKING

TECHNICAL FIELD

The present invention relates to an inorganic composition having excellent zinc ion sustained-release properties that can be used as an active ingredient for pharmaceuticals and a method for manufacturing the same.

BACKGROUND ART

In JP 2004-161684 A, claim 1 describes "a wound healing film formulation in which a physiological active substance having a wound healing promoting activity is blended into a substrate of a water-soluble polymer selected from gelatin, pectin, polyvinylpyrrolidone, polyvinyl alcohol, and sodium polyacrylate". In one aspect, the adhesive used in the film formulation is a mixture of aluminum salts, poorly soluble metal salts and/or poorly soluble metal oxides, and examples of metal salts and/or metal oxides include zinc carbonate, zinc oxide, and the like (paragraph [0026]).

In JP 2005-6995 A, claim 1 describes "a material for skin contact comprising an acid-modified conjugated diene-based polymer containing 0.01 to 5 mmol/g of at least one type of acidic functional group selected from the group of carboxylic acid (salt) group, sulfonic acid (salt) group, and phosphoric acid (salt) group". The acid-modified conjugated diene polymer may include a crosslinking agent for covalent bonding and a crosslinking agent for ionic bonding as a crosslinking agent, and as the ionic crosslinking agent, zinc carbonate and zinc oxide are described (paragraph [0022]).

Zinc is believed to be a substance that provides $Zn^{2+}$ ions to a wound site when used as a therapeutic agent for a skin wound or skin roughness. A technique with which $Zn^{2+}$ ions can be appropriately supplied to a wound site and the substance can be supplied as an inorganic composition having excellent stability from the perspective as an active ingredient for pharmaceuticals, and in addition, which allows the supply by a simple and convenient manufacturing method, is desired.

CITATION LIST

Patent Literature

Patent Document 1: JP 2004-161684 A
Patent Document 2: JP 2005-6995 A

SUMMARY OF INVENTION

Technical Problem

An object of the invention is to provide an inorganic composition that is useful as an active ingredient for pharmaceuticals and has excellent stability, and a method for manufacturing the same.

Solution to Problems

An active ingredient of the pharmaceuticals mentioned herein below is characterized as being inorganic compound compositions that can be used in the pharmaceuticals described below. Generally, inorganic compound compositions which contain zinc are of a plate-like shape and they are known to be used in cosmetics (applications to the skin) utilizing their concealing properties. However, to be used as an active ingredient for pharmaceuticals, a plate-like shape may cause a risk of cytotoxicity, and thus, it is preferably an atypical shape, an ellipsoid shape, or a substantially spherical shape without sharp parts with a particle size of 50 to 0.1 μm, and more preferably a particle size of 10 to 1 μm. More preferably, depending on the application of the pharmaceutical product, adjustments such as particle size, surface area, particle size distribution, may be made so that the sustained-release of zinc ions from the pharmaceuticals can be appropriately controlled.

The present description discloses, as pharmaceuticals, a therapeutic agent for a skin wound or skin roughness, a medical device having a therapeutic agent and a covering material, and a set in which a therapeutic agent and a covering material are combined. The invention describes an inorganic composition having excellent zinc ion sustained-release properties that can be used as an active ingredient of these pharmaceuticals, and a method for manufacturing the same.

(Inorganic Composition Having Excellent Zinc Ion Sustained-Release Properties that can be Used as an Active Ingredient for Pharmaceuticals)

(1) An inorganic composition having an excellent zinc ion sustained-release property, which can be used as an active ingredient of a pharmaceutical, comprising at least one selected from the group consisting of zinc sulfate, zinc chloride, zinc carbonate, zinc hydroxide, and zinc oxide.

(2) An inorganic composition having an excellent zinc ion sustained-release property, which can be used as an active ingredient of a pharmaceutical, wherein the zinc carbonate comprises at least one selected from the group consisting of zinc carbonate, zinc carbonate hydroxide, and zinc carbonate hydroxide hydrate.

(3) The inorganic composition having an excellent zinc ion sustained-release property, which can be used as an active ingredient of a pharmaceutical comprising not less than 0.1 mass % and less than 1.5 mass % of sulfur as S as a result of at least partial substitution of carbonate ions with $SO_4^{2-}$ ions.

(4) The inorganic composition having an excellent zinc ion sustained-release property, which can be used as an active ingredient of a pharmaceutical comprising not less than 0.05 mass % and less than 1 mass % of chlorine as Cl as a result of at least partial substitution of carbonate ions with $Cl^-$ ions.

(5) The inorganic composition having an excellent zinc ion sustained-release property according any one of (2) to (4), which can be used as an active ingredient of a pharmaceutical, wherein the zinc carbonate hydroxide hydrate comprises hydrozincite, and at least one of the hydrozincite-containing zinc carbonate hydroxide hydrates selected from the group consisting of the zinc carbonate hydroxide hydrate comprising not less than 0.1 mass % and less than 1.5 mass % of sulfur as S as a result of at least partial substitution of carbonate ions with $SO_4^{2-}$ ions and the zinc carbonate hydroxide hydrate comprising not less than 0.05 mass % and less than 1 mass % of chlorine as Cl as a result of at least partial substitution of carbonate ions with $Cl^-$ ions has an amount of dissolved $Zn^{2+}$ ions of not less than 0.1 μg/m² and pH of not less than 7.2 and less than 8.3 after a dissolution test using stirring method;

where, in the dissolution test, a BET specific surface area of the hydrozincite-containing zinc carbonate hydroxide hydrate is from 10 to 150 m²/g, a mass ratio of the hydrozincite-containing zinc carbonate hydroxide hydrate to the saline is 1:50, and a time for stirring at 37° C. using a rotor at 500 rpm is 3 hours.

(6) The inorganic composition having an excellent zinc ion sustained-release property according to any one of (2) to (5), which can be used as an active ingredient of a pharmaceutical, wherein the hydrozincite-containing zinc carbonate hydroxide hydrate is represented by Formula (1) below, and the molar ratio of Zn to $CO_3$ is $Zn/CO_3=2.5-3.3$;

$$Zn_{4-6}(CO_3)_{1-3}(OH)_{5-6} \cdot nH_2O \quad (1)$$

where n is 0 to 6.

(7) The inorganic composition having an excellent zinc ion sustained-release property according to any one of (3) to (5), which can be used as an active ingredient of a pharmaceutical, wherein the zinc carbonate hydroxide hydrate comprising the hydrozincite and not less than 0.1 mass % and less than 1.5 mass % of sulfur as S is represented by Formula (2) below, and the molar ratio of Zn to $((1-x)CO_{3-x}(SO_4))$ is $Zn/(1-x)CO_{3+x}(SO_4))=2.5-3.3$;

$$Zn_{4-6}((1-x)CO_{3+x}(SO_4))_{1-3}(OH)_{5-6} \cdot nH_2O \quad (2)$$

where n is 0 to 6, And X is 0.005 to 0.1.

(8) The inorganic composition having an excellent zinc ion sustained-release property according to (4) or (5), which can be used as an active ingredient of a pharmaceutical, wherein the zinc carbonate hydroxide hydrate comprising the hydrozincite and not less than 0.05 mass % and less than 1 mass % of chlorine as Cl is represented by Formula (3), and the molar ratio of Zn to $((1-x)CO_{3+x}Cl)$ is $Zn/((1-x)CO_{3-x}Cl)=2.5-3.3$;

$$Zn_{4-6}((1-x)CO_{3+x}Cl)_{1-3}(OH)_{5-6} \cdot H_2O \quad (3)$$

where n is 0 to 6, and x is 0.005 to 0.1.

(9) The inorganic composition having an excellent zinc ion sustained-release property according to any one of (6) to (8), which can be used as an active ingredient of a pharmaceutical, wherein the hydrozincite-containing zinc carbonate hydroxide hydrate represented by the chemical formula of the Formula (1), Formula (2), or Formula (3) is a zinc carbonate hydroxide hydrate comprising not less than 0.1 mass % and less than 1.5 mass % of sulfur as S as a result of at least partial substitution of carbonate ions with $SO_4^{2-}$ ions, or a zinc carbonate hydroxide hydrate comprising not less than 0.05 mass % and less than 1 mass % of chlorine as Cl as a result of at least partial substitution of carbonate ions with $Cl^-$ ions, in whose XRD diffraction pattern, a structure of $Zn_5(CO_3)_2(OH)_6 \cdot nH_2O$, $Zn_5((1-x)CO_{3+x}SO_4)_2(OH)_6 \cdot nH_2O$, or $Zn_5((1-x)CO_{3+x}Cl)_2(OH)_6 \cdot nH_2O$ (for each chemical formula, x is 0.005-0.1 and n is 0-6) is dominant; where, a axis is 13.3 to 13.8, b axis is 6.2 to 6.4, c axis is 5.25 to 5.5, and β is 94.9 to 97.5.

(10) The inorganic composition having an excellent zinc ion sustained-release property according to any one of (6) to (9), which can be used as an active ingredient of a pharmaceutical, wherein the pharmaceutical is a therapeutic agent for a skin wound or skin roughness, and when the therapeutic agent is dissolved in saline and used, a ratio of the pharmaceutical to saline is from 0.1 g/L to 100 g/L, and the inorganic composition is represented by the formula of any one of the formulae (1) to (3), and when n==0 (anhydrous), the zinc concentration relative to a total amount of the pharmaceutical is from 45 mass % to 75 mass % as metal zinc, and the zinc concentration in the saline of the pharmaceutical is from 0.045 g/L to 75 g/L.

(11) The inorganic composition having an excellent zinc ion sustained-release property according to any one of (1) to (10), which can be used as an active ingredient of a pharmaceutical, wherein the pharmaceutical is a therapeutic agent for a skin wound or skin roughness, and the skin wound or skin roughness is a skin wound or skin roughness which reaches up to the dermis via the epidermis, or pressure ulcers, a skin wound or skin roughness which reaches up to peritoneum via epidermis and dermis.

(12) The inorganic composition having an excellent zinc ion sustained-release property according to (10) or (11), which can be used as an active ingredient of a pharmaceutical, wherein the therapeutic agent is in a form of powder, lotion, solution, cream, ointment, spray, or gel and is applied or sprayed to a part of a skin wound or a skin roughness to be utilized.

(13) The inorganic composition having an excellent zinc ion sustained-release property that can be used as an active ingredient of a pharmaceutical according to any one of (1) to (12), wherein the pharmaceutical is a medical device comprising a wound covering material retaining the therapeutic agent and the skin wound or skin roughness in a closed environment.

(14) The inorganic composition having an excellent zinc ion sustained-release property according to (13), which can be used as an active ingredient of a pharmaceutical, wherein the wound covering material is at least one selected from the group consisting of polyurethane film dressing material, hydrocolloid dressing material, polyurethane foam dressing material, alginate covering material, hydrogel dressing material, hydropolymers, cellulose film, and silk film.

(15) The inorganic composition having an excellent zinc ion sustained-release property according to any one of (10) to (14), which can be used as an active ingredient of a pharmaceutical, wherein the therapeutic agent for a skin wound or skin roughness is present by being applied to, contained in, or adhered to the wound covering material.

(16) The inorganic composition having an excellent zinc ion sustained-release property according to any one of (10) to (14), which can be used as an active ingredient of a pharmaceutical, wherein the wound covering material is made to carry the therapeutic agent when manufactured, or the therapeutic agent is fixed through spray, immersion, or application to an application side surface of the wound covering material that has been processed into a sheet form, whereby the therapeutic agent and the wound covering material are used as a medical device.

(17) The inorganic composition having an excellent zinc ion sustained-release property according to any one of claims 1 to 12, which can be used as an active ingredient of a pharmaceutical, wherein the pharmaceutical is a combined set of a therapeutic agent for a skin wound or skin roughness comprising the inorganic composition having an excellent zinc ion sustained-release property that can be used as an active ingredient of a pharmaceutical, and a wound covering material.

(Method for Manufacturing an Inorganic Composition Having Excellent Zinc Ion Sustained-Release Properties that can be Used as an Active Ingredient for Pharmaceuticals)

For the ultimate use as an active ingredient for pharmaceuticals, the manufacturing method described below comprises: a step of crushing for adjusting preferably into an atypical shape, an ellipsoid shape, or a substantially spherical shape without sharp parts with a particle size of 50 to 0.1 μm, and more preferably a particle size of 10 to 1 μm, or a step of adjusting the particle size using a ball mill or the like (including granulation).

(18) A method of manufacturing the inorganic composition according to any one of (1) to (12), comprising maintaining an almost constant pH by acid or alkali in the presence of aqueous solution including carbonate ions, continuously supplying zinc ions from an aqueous zinc solution, and precipitating zinc carbonate hydroxide having a main component of hydrozincite. Here, the "almost constant pH" is not particularly limited, and preferably ±1 of a predetermined pH and more preferably ±0.3 of a predetermined pH. The "main component of hydrozincite" means that hydrozincite is the most dominant component in basic zinc carbonate. In the present description, basic zinc carbonate may also be referred to as zinc carbonate hydroxide.

(19) The method of manufacturing the inorganic composition according to (1), wherein the pH is greater than 6 and less than 11 and a temperature is lower than 40° C.

(20) The method of manufacturing the inorganic composition according to (18) or (19), wherein the zinc ion donor is at least one selected from the group consisting of zinc nitrate, zinc chloride, and zinc sulfate.

(21) The method of manufacturing the inorganic composition according to any one of (18) to (20), wherein the carbonate ion donor is at least one selected from the group consisting of sodium hydrogen carbonate and ammonium carbonate.

Advantageous Effects of Invention

The invention is of an inorganic composition having excellent zinc ion sustained-release properties that can be used as an active ingredient for pharmaceuticals and having excellent stability as an active ingredient of pharmaceuticals, and in addition, the manufacturing method of which is simple and convenient.

BRIEF DESCRIPTION OF DRAWINGS

FIG. 2 shows schematic views showing the states where a full thickness skin loss is applied with powder of Preparation Example 1 and then covered by a covering material.

FIG. 3 shows schematic views of a wound having been just produced and the wound after a while, for showing the reepithelization rate.

FIG. 4 is a view for explaining a measurement method of the reepithelization rate.

FIG. 5 shows micrographs of cross sections of skin for showing histological observation results of a wound having been just produced and the wound after a while.

FIG. 7 shows schematic views for describing a healing process of a wound or a burn.

DESCRIPTION OF EMBODIMENTS

Figure 1:
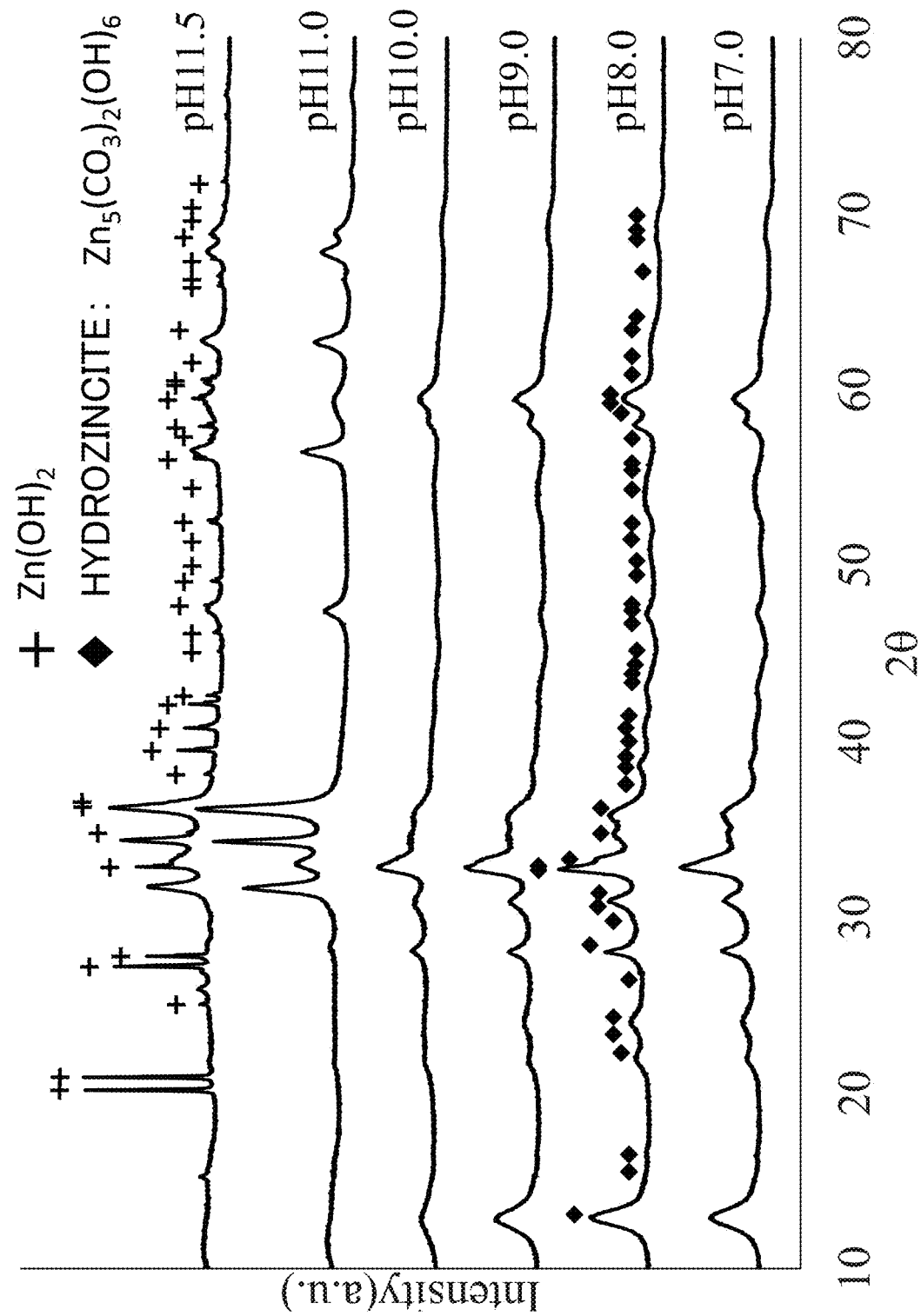
FIG. 1 is a chart of XRD (X-ray diffraction) of hydrozincite obtained by the method for manufacturing a Preparation Example of the invention. pH is the pH when synthesized.

1. Summary of Inorganic Composition of the Invention (1) The inorganic composition of the invention is an inorganic composition that can be used as an active ingredient for a therapeutic agent for a skin wound or skin roughness as the pharmaceuticals described below.

The inorganic composition is preferably used when the skin wound or skin roughness is a pressure ulcer where the skin wound or skin roughness reaches up to the peritoneum via the epidermis and dermis, or used for skin wound and skin roughness.

The therapeutic agent for a skin wound or skin roughness as pharmaceuticals preferably has an amount of dissolved $Zn^{2+}$ ions of not less than 0.1 μg/m² and pH of not less than 7.2 and less than 8.3, and more preferably an amount of dissolved $Zn^{2+}$ ions of 0.5 μg/m² and pH of not less than 7.2 and less than 8.3 after a dissolution test by the stirring method explained hereinafter.

(Dissolution Test by Stirring Method)

The amount of dissolved $Zn^{2+}$ ions is measured in the present description as follows: The surface areas of samples, which are produced with varying pH values at production by the same process as that for Preparation Example 2 of Examples to be described later, are measured beforehand by the BET method (BET specific surface area analyzer: High Precision, Multi-Analyte Gas Adsorption Analyzer, available from Quantachrome Instruments Japan G.K.). For each sample, the $Zn^{2+}$ ion concentration after stirring in saline is measured by an ICP emission spectrometer (ICPE-9000, available from Shimadzu Corporation) to thereby obtain the amount of dissolved $Zn^{2+}$ ions, and the amount of dissolved $Zn^{2+}$ ions is divided by the surface area previously measured. The mass ratio of each sample to saline is set to 1:50 and the amount of $Zn^{2+}$ ions dissolved in the saline is measured after stirring at 37° C. for 3 hours at 500 rpm using a rotor.

(2) The active ingredient of the pharmaceuticals may be used as a pharmaceutical alone, or it may be used together with a suitable carrier.

(2-1) The pharmaceuticals can be used as a medical device for treating skin wound or skin roughness as well as a wound covering material that retains the inorganic composition and the skin wound or skin roughness in a closed environment. The inorganic composition is preferably coated, impregnated, or adhered to a wound covering material that retains the therapeutic agent for a skin wound or skin roughness in a closed environment.

(2-2) In another aspect, the pharmaceuticals may be used as a medical set for treating a skin wound or skin roughness, which is a combination of a therapeutic agent for a skin wound or skin roughness containing an inorganic composition that can be used as an active ingredient of pharmaceuticals, with the above-mentioned wound covering material.

2. Specific Description of Inorganic Composition of the Invention

The inorganic composition according to the invention is an inorganic composition comprising at least one selected from the group consisting of zinc sulfate, zinc chloride, zinc carbonate, zinc hydroxide, and zinc oxide.

Zinc carbonate is a carbonate of zinc, which is used as an abbreviation for basic zinc carbonate or zinc carbonate hydroxide. The chemical formula thereof is $ZnCO_3$, but the composition is not stable and is generally represented by the chemical formula $2ZnCO_3 \cdot 3Zn(OH)_2 \cdot H_2O$ in the industrial field. Generally, it refers to a basic zinc carbonate. In nature, it exists as smithsonite.

Zinc carbonate is an inorganic composition containing at least one selected from the group consisting of zinc carbonate, zinc carbonate hydroxide, and zinc carbonate hydroxide hydrate.

The inorganic composition of the invention may be natural or commercially available zinc carbonate, zinc sulfate, zinc chloride, zinc hydroxide, zinc oxide, or may be synthesized, or may be a mixture of them. Zinc oxide is described as pharmaceuticals in the Japan Pharmacopoeia.

The inorganic composition of the invention may be obtained using a precipitate produced by an alkali precipitation method from an aqueous zinc salt solution. Preferably, in the precipitate generation reaction described below, a precipitate obtained by the reactions of $Zn^{2+}$ ions, $(CO_3)^{2-}$ ions, and $OH^-$ ions in a reaction field where the pH is controlled preferably not less than 6.5 and less than 9.5, more preferably not less than 7.0 and less than 9.5 is used as the inorganic composition of the invention. More preferably, it is a hydrozincite-containing zinc carbonate hydroxide hydrate represented by Formula (1) below.

$$Zn_{4-6}(CO_3)_{1-3}(OH)_{5-6} \cdot nH_2O \quad (1)$$

where n is 0 to 6. Its chemical formula is also represented as $Zn_5(CO_3)_2(OH)_4$.

Alternatively, a precipitate obtained by the reactions of $Zn^{2+}$ ions, $(CO_3)^{2-}$ ions, $(SO_4)^{2-}$ ions, and $OH^-$ ions in a reaction field where the pH is controlled at not less than 7.0 and less than 9.5 is used as the inorganic composition of the invention. More preferably, it is a zinc carbonate hydroxide hydrate containing hydrozincite and not less than 0.1 mass % and less than 1.5 mass % of sulfur as S, represented by Formula (2) below.

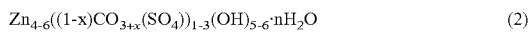
$$Zn_{4-6}((1-x)CO_{3+x}(SO_4))_{1-3}(OH)_{5-6} \cdot nH_2O \quad (2)$$

where n is 0 to 6, and x is 0.005 to 0.1.

Furthermore, a precipitate obtained by the reactions of $Zn^{2+}$ ions, $(CO_3)^{2-}$ ions, $Cl^-$ ions, and $OH^-$ ions in a reaction field where the pH is controlled at not less than 7.0 and less than 9.5 is used as the inorganic composition of the invention. More preferably, it is a zinc carbonate hydroxide hydrate containing hydrozincite and not less than 0.05 mass % and less than 1 mass % of chlorine as Cl, represented by Formula (3) below.

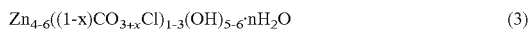
$$Zn_{4-6}((1-x)CO_{3+x}Cl)_{1-3}(OH)_{5-6} \cdot nH_2O \quad (3)$$

where n is 0 to 6, and x is 0.005 to 0.1.

3. Method of Manufacturing the Inorganic Composition of the Invention

The inorganic composition of the invention is a composition comprising at least one selected from the group consisting of zinc sulfate, zinc chloride, zinc carbonate, zinc hydroxide, and zinc oxide. To a $NaH(CO_3)$ aqueous solution as a preferable carbonate source used in the alkali precipitation method, NaOH is added dropwise as a mineralization material so that the pH of the aqueous solution is preferably maintained at not less than 6.5 and less than 9.5, more preferably from not less than 7.0 and less than 9.5, and then, an aqueous solution of zinc such as acidic zinc nitrate is added dropwise to form a precipitate, and after stirring for 10 to 30 hours, solid-liquid phase separation is carried out by suction filtration or centrifugation, and once washed with distilled water and the like, the precipitate is vacuum dried to obtain a zinc carbonate hydroxide hydrate having hydrozincite as a main component. The particle size of the obtained zinc carbonate hydroxide hydrate is not limited, and when used as an active ingredient for pharmaceuticals, the particle size can be set appropriately by a known method.

The carbonate source, the zinc source, and the mineralization material as the ingredients are not limited to those described above. The carbonate source includes $(NH_4)CO_3$, $Na_2CO_3$, preferably $NaH(CO_3)$ aqueous solution, and the zinc source is selected from zinc sulfate, zinc chloride, zinc acetate and zinc nitrate, while $NH_3$ or NaOH aqueous solution is used as the mineralization material. The carbonate source aqueous solution and the zinc source aqueous solution are preferably reacted at a concentration ratio (molar ratio) of carbonate to zinc of 2:5, and the concentration of the zinc source in aqueous solution is preferably in a range from 0.1 to 1 M. The reaction is performed at a temperature of 40° C. or lower, and preferably at 25° C. The obtained zinc carbonate hydroxide hydrate having hydrozincite as a main component is a mixture of a reaction product obtained by a precipitate generation reaction of an aqueous zinc salt solution and an aqueous alkali solution, ingredients as unreacted substances, by-products, and impurities contaminated from ingredients.

FIG. 1 shows an XRD chart of hydrozincite manufactured with varying pH conditions as shown in Preparation Example 2, which will be described later in the examples. As for the XRD device, D8 ADVANCE available from Bruker Corporation is used.

As shown in the cases of pH 7.0 to 10.0 in the chart in FIG. 1, at the XRD diffraction peaks of hydrozincite-containing zinc carbonate hydroxide hydrate, the structure of $Zn_5(CO_3)_2(OH)_6 \cdot nH_2O$ [Formula (1)] of hydrozincite marked with a peak in the case of pH 8.0 in the chart is dominant, and at this point, it is preferable that a axis is 13.6 to 14.0, b axis is 6.25 to 6.4, c axis is 5.3 to 5.4, and β is 95.0 to 97.5. In addition, the case of substitution of carbonate ions with $SO_4^{2-}$ ions or $Cl^-$ ions in the structure of hydrozincite is shown in the above-mentioned Formula (2) or (3), respectively, and it is preferable that a axis is 13.3 to 13.8, b axis is 6.2 to 6.4, c axis is 5.25 to 5.5, and β is 94.9 to 97.5. A pharmaceutical as therapeutic agent for a skin wound or skin roughness is highly effective when its crystal has the XRD diffraction peaks within this range.

Additionally, in Table 1, the XRD diffraction results of zinc carbonate hydroxide hydrate containing not less than 0.1 mass % and less than 1.5 mass % of sulfur as S as a result of substitution of carbonate ions with $SO_4^{2-}$ ions and zinc carbonate hydroxide hydrate containing not less than 0.05 mass % and less than 1 mass % of chlorine as Cl as a result of substitution of carbonate ions with $Cl^-$ ions, manufactured by the manufacturing methods described in Preparation Examples 3 and 4 respectively, are shown together with the XRD diffraction result of hydrozincite shown in the XRD chart of FIG. 1, as the relationship of pH at synthesis and the identified mineral phase.

TABLE 1

| | pH at synthesis | | | | |
|---|---|---|---|---|---|
| | 6 | 6.5 | 7 | 7.5 | 8 |
| Preparation Example 2 | — | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite |
| Preparation Example 3 | — | $Zn_{12}(CO_3)_3(SO_4)(OH)_{16}$ Bryangite | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite |
| Preparation Example 4 | — | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite |

| | pH at synthesis | | | |
|---|---|---|---|---|
| | 8.5 | 9 | 9.5 | 10 |
| Preparation Example 2 | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite | $Zn_5(CO_3)_2(OH)_6$ Hydrozincite |
| Preparation Example 3 | $Zn_5(CO_3)_2(OH)_6$ Hydrozincite | $Zn_5(CO_3)_2(OH)_6$ Hydrozincite | | |
| Preparation Example 4 | $Zn_5(CO_3)_2(OH)_6$ Hydrozincite | $Zn_5(CO_3)_2(OH)_6$ Hydrozincite | | |

While the manufacturing conditions under which a hydrozincite becomes a main component vary depending on the type and concentration of the carbonate source and the zinc source used, by varying the pH conditions and maintaining each pH condition to be constant for the manufacture, an optimal pH condition can be found. Here, the main component refers to the most abundant component in the mixture, and it is preferably not less than 80 mass %, and more preferably not less than 95 mass %.

4. Method for Manufacturing Zinc Oxide

In another aspect of the inorganic composition that can be used as an active ingredient for the pharmaceuticals of the invention, zinc oxide can be obtained by heat treating a precipitate obtained by the alkaline precipitation method described above at a temperature of not lower than 700° C., preferably from 1000° C. to 1300° C., the obtained zinc oxide has characteristics of excellent heat resistance, durability and safety as an inorganic antimicrobial composition, and its antimicrobial effect is high as an inexpensive inorganic antimicrobial agent that expresses an effect even in the dark. It may be mixed with a therapeutic agent for a skin wound or skin roughness and used. Zinc oxide has a drying effect as well as antimicrobial properties, and thus, it is highly stimulative. Therefore, when mixed and used in a hydrozincite-containing zinc carbonate hydroxide hydrate of the invention, an amount of zinc oxide, converted to an amount of metal zinc, is preferably no greater than 30 mass %, and more preferably no greater than 10 mass % of the total amount of metal zinc.

5. Inorganic Composition with Excellent Zinc Ion Sustained-Release Properties

To date, a number of studies have been conducted to apply zinc compounds such as $ZnSO_4$, $ZnCl_2$, and ZnO to wound sites created in experimental animals to evaluate wound healing effects. These compounds are substances that supply $Zn^{2+}$ ions to the wound site. Meanwhile, it has been reported that there is an optimal concentration of $Zn^{2+}$ ions for obtaining wound healing effects of $Zn^{2+}$ ions. If the concentration is not more than 500 μmol/L, no toxicity is caused with respect to fibroblasts; however, the presence of zinc ions at a high-level concentration (not less than 15 mmol/L) is known to increase inflammatory cell infiltration of skin and to significantly delay re-epithelialization.

In addition, pH of a body fluid having saline as a main component is maintained at approximately 7.4 to 7.5, and when a basic zinc carbonate or the like having hydrozincite of the invention as a main component is dissolved in saline, variation of pH that corresponds to generation and dissolution of the $Zn^{2+}$ ions is expected. Furthermore, by deciding on the following 2 states, i.e., the pH environment for supplying $Zn^{2+}$ ions and/or $(CO_3)^{2-}$ ions and the supply of $OH^-$ ions for efficiently activating the matrix metalloprotease (MMPs) enzymes that decompose substrate proteins via OH-ions of the water molecules, the treatment is further promoted, and tissues that interfere with the treatment of scab or the like would not be formed, the scar remaining is prevented, and thus, the patient's QOL (Quality of Life) can be expected to improve.

In the wound healing process, it is known that active proliferation and migration of cells occur. When cells migrate into or between tissues, the existing extracellular matrix has to be locally disrupted. A new extracellular matrix is formed simultaneously to reconstruct the tissue at the wound site. Various proteolytic enzymes are involved in these processes.

The active balance of matrix metalloproteases (MMPs) and tissue inhibitory metalloproteases (TIMPs) is responsible for both normal and pathological events, such as wound healing, tissue repair, angiogenesis, infiltration, tumor formation, and metastasis.

MMP is an enzyme that decomposes extracellular collagen and is synthesized by cells that are present between connective tissues. MMP has a zinc ion in the center and there is a $Zn^2$ ion binding site at the active site. Epidermal regeneration is achieved by the epidermis cells migrating from wound edges and skin appendages (hair root, sweat glands, etc.). Thus, binding of $Zn^2$ ions from the zinc compound with MMPs causes destruction of the extracellular matrix and promotes epidermal cell migration.

TIMP is an enzyme that is produced by fibroblasts, endothelial cells, and the like, and has an inhibitory effect against MMP. MMP and TIMP form a complex in a ratio of 1:1, and thus the collagen decomposition of MMPs is inhibited. This mechanism can facilitate fiber formation at the wound site by inhibiting specific cleavage of the helix site of the type I, II and III collagens caused by MMPs, and thus, can increase the amount of collagen in the regenerated tissue.

As stated above, it is believed that the inorganic composition having an excellent zinc ion sustained-release property that can be used as an active ingredient for the pharmaceuticals of the invention can promote cell migration by appropriately providing zinc ions to the wound site as pharmaceuticals, and can increase collagen accumulation and promote wound healing.

Furthermore, by focusing on a pH environment for supplying zinc ions and/or carbonate ions, the treatment is further promoted, and tissues that interfere with the treatment, such as scab, would not be formed, the scar remaining is prevented, and thus, the patient's QOL (Quality of Life) can be expected to improve.

The therapeutic agent for a skin wound or skin roughness as the pharmaceuticals using the inorganic composition of the invention is not limited but can treat skin wounds or skin roughness, which is a defect in epidermis and dermis (of full thickness skin). Here, the skin wound or skin roughness is a skin wound or skin roughness which reaches up to dermis via epidermis, or pressure ulcers, skin wound, or skin roughness which reaches up to peritoneum via epidermis and dermis.

Clinically, pressure ulcers are those produced when the patient becomes bedridden and the like staying at the same position over a long period of time, which results in an impaired blood circulation at the contact site between the body and a supporting face (most often, a bed), causing necrosis in the peripheral tissues. It is also commonly referred to as bedsores.

This will be described using the schematic views shown in FIG. 7.

FIG. 7A is a schematic view showing a cross-section of the skin, and "1" represents a skin wound, pressure ulcer, or skin roughness which reaches up to dermis via epidermis. In a dry environment in which the wound is dry, the therapeutic agent of the invention is applied to the inner surface of the wound, and when scab such as eschar is formed, the upper surface of the wound is protected by a breathable adhesive plaster or the like. As shown in FIG. 7B, at the inner surface of the wound, epidermal cells grow as the wound heals. As shown in FIG. 7C, when the healing further progresses, the fibroblasts cover the wounds, and the scar tissue develops and heals on the upper surface of the wound.

In a moist environment where an exudate shown is present and the wound is moist as shown in FIG. 7D, the upper part of the wound is covered with a water absorbing wound covering material as described below, and the therapeutic agent of the invention is applied to the surface of the wound. In such an environment, the medical device of the invention can provide an optimal environment for granulation and epithelial cell migration. As shown in FIG. 7D, epidermal cells grow on the surface or inner surface of the wound as the wound heals. As shown in FIG. 7E, when the healing further progresses, the fibroblasts cover the wounds, and the skin tissue develops on the upper surface of the wound so that the wound heals.

6. Other Applications (1) Pharmaceuticals for Use with Wound Covering Materials

The inorganic composition having excellent zinc ion sustained-release properties that can be used as an active ingredient for pharmaceuticals of the invention can be used as a pharmaceutical in combination with wound covering materials. The wound covering material is capable of retaining the therapeutic agent for a skin wound or skin roughness which is the pharmaceutical according to the invention in a closed environment.

The wound covering materials that can be used are described below.

Healing of skin wounds or skin roughness may involve healing in a dry environment and in a moist environment. When healing in a dry environment, no wound covering material may be used in some cases, but generally the wound or the skin roughness is covered with a breathable wound covering material for protection. Gauze, bandages, and breathable film-like wound covering materials may be used.

The therapeutic agent for a skin wound or skin roughness can be brought in a closed environment with wound covering materials and be also retained in a suitable moist environment, thereby being therapeutically effective. When an inorganic composition which is the inorganic material described above is combined with the wound covering material which is an organic material, a large synergistic effect can be obtained by hybridizing the organic and inorganic materials.

When the active ingredient of the invention is used as a pharmaceutical, saline or the like is used as a solvent to make a liquid drug for use in the form of, for example, lotion, solution, cream, ointment or spray. Furthermore, the active ingredient can also be used in a powder dosage form when exudate is present in the wound and the wound is moist. If necessary, it may be made into a thickening state or gel agent (sometimes referred to as a gel) which is an intermediate state of the above.

The therapeutic agent for a skin wound or skin roughness of the invention can be brought in a closed environment with wound covering materials and be also prepared in a dosage form of liquid or powder so as to maintain each wound in a suitable moist state, thereby being therapeutically effective in a moist environment. In either of the dosage forms of liquid or powder, the therapeutic agent as a pharmaceutical used with the wound covering material provide a high QOL (Quality of life) to the patient because the tissues that interfere with the treatment such as scab would not be formed, and the scar remaining is prevented.

<Medical Device Comprising Therapeutic Agent and Wound Covering Material>

In another aspect, the therapeutic agent of the invention may be carried in the covering material in the manufacture of the wound covering material so as to be used in a medical device. This may be a medical device in which the therapeutic agent of the invention is applied to, contained in, or adhered to the wound covering material and the wound covering material retains the skin wound or the skin roughness in a closed environment. The therapeutic agent is contained and deposited when the wound covering material is synthesized.

Alternatively, the therapeutic agent may be fixed by spraying, immersing, or applying the therapeutic agent to the application side surface of the wound covering material that has been processed into a sheet form, and then used as a medical device.

<Wound Covering Material>

Examples of the wound healing materials can include, polyurethane film dressing material, a hydrocolloid dressing material, polyurethane foam dressing material, alginate covering material, hydrogel dressing material, hydropolymers, chitin wound covering material, and silk film, but are not limited thereto.

For details of the wound covering materials that are used with the inorganic composition of the invention as pharmaceuticals, reference can be made to the description in paragraphs [0038] to [0045] of an international application, PCT/JP2016/067416 filed by the present applicant concerning the case where used along with the inorganic composition of the invention.

For example, a chitin wound covering material is described below as an example that is not described in the above international application.

The chitin would covering material is obtained by removing calcium or proteins which become an allergen from a shell of a crustacean and purifying the resultant to obtain amino polysaccharides, which are formed into a sheet form. This has a high bioaffinity, and analgesic and hemostatic effects can be expected. While the material has an excellent water absorption and allows the retention of moist environments, secondary dressing materials are needed. The chitin processed into a cotton form is thick, and when a large amount of exudate is present, it is replaced daily, and when the amount is reduced, the time till replacement is extended. A gauze coated with the sponge-like processed chitin is also useful.

The therapeutic agents of the invention can be pharmaceutical sets with these wound covering materials.

The form of use (treatment technique) as a pharmaceutical at this time is as follows.

The active ingredient of the invention may be a therapeutic agent for a skin wound or skin roughness as a pharmaceutical, and may include a pharmaceutically acceptable carrier, if necessary. Examples of the carrier include organic powders, inorganic powders, organic solvents and inorganic solvents, more specifically, corn starch, cereal flour, talc, water, saline, alcohols, polyhydric alcohols, or mixtures thereof. To have a form of the pharmaceutical, a thickening agent or the like may be added, and the ingredient is processed into a gel form or a paste form having the improved handleability.

<Carriers Used in Therapeutic Agent>

Examples of the carrier include hydrocarbons such as alpha-olefin oligomers, paraffin waxes, ceresin, microcrystalline wax, animal and vegetable oils such as persic oil, olive oil, beef fat, and mink oil, synthetic esters such as cetyl octanoate, isopropyl myristate, and cetyl palmitate, natural animal and vegetable waxes such as jojoba oil, carnauba wax, candelilla wax, Japan wax, and beeswax, silicone oils and derivatives thereof such as sorbitan stearate, polyoxyethylene glyceryl tristearate, polyoxyethylene lauryl ether, decaglyceryl trioleate, sucrose monolaurate ester, dimethylpolysiloxane, and methylphenyl polysiloxane, and the like.

Fluororesins such as perfluoropolyether, alcohols such as ethanol, 1,3-butylene glycol, propylene glycol, and diglycerin; carrageenan, xanthan gum, sodium carboxymethylcellulose, collagen, elastin, silk, cellulose, lactoferrin and other proteins and hydrolysates thereof, powders of anhydrous silicic acid, nylon powder, polyalkyl acrylate, alumina, and iron oxide may be used.

In addition, ultraviolet absorbers, vitamins, ureas, dried-seawater products, anti-inflammatory agents, amino acids and derivatives thereof, lecithin, colorants, perfumes, preservatives, and the like, oils such as egg yolk oil, macadamia nut oil, cottonseed oil, avocado oil, coconut oil, palm oil, palm kernel oil, corn oil, peanut oil, beef fat, and carnauba wax can be used.

Still others include beeswax, liquid paraffin, lanolin, squalane, stearic acid, laurate esters, myristic acid esters, isostearyl alcohol, purified water, electrolyzed water, ethyl alcohol and the like. That is, in general, those commonly blended in cosmetic products and quasi drugs can be used as the carrier in the therapeutic agent for a skin wound or skin roughness of the invention. The carrier may not be used.

For example, other components that may be added to the therapeutic agent for a skin wound or skin roughness of the invention are selected depending on those to be actually added in cosmetics or quasi drug. Although it cannot be strictly distinguished, humectants include glycerin, sorbitol, polyethylene glycol, pyrrolidone carboxylic acid and salts thereof, collagen, 1,3-butylene glycol, hyaluronic acid and salts thereof, chondroitin sulfate and salts thereof, xanthan gum, and the like.

Antioxidants include ascorbic acid, α-tocopherol, dibutylhydroxytoluene, parahydroxyanisole, and the like. Surfactants include sodium stearyl sulfate, diethanolamine cetyl sulfate, polyethylene glycol monostearate, ethylene glycol monostearate, polyoxyethylene hydrogenated castor oil, soybean lysophospholipid solution, polyoxyethylene sorbitan monooleate, and the like.

Preservatives include inorganic pigments such as phenoxyethanol, ethylparaben, butylparaben, zinc oxide, and the like.

Anti-inflammatory agents include glycyrrhizinic acid derivatives, salicylic acid derivatives, hinokitiol, zinc oxide, allantoin, and the like.

Whitening agents include placenta extract, glutathione, saxifraga extract, ascorbic acid derivatives, arbutin, and the like.

Blood circulation promoters include γ-oryzanol, sodium dextran sulfate, and the like.

Antiseborrheic agents include sulfur, thianthol, and the like.

Examples of thickening agents include carboxyvinyl polymers and the like.

pH adjusting agents include lactic acid, citric acid, malic acid, glycolic acid, sodium hydroxide, hydrotalcite, and the like.

(2) Effect as a Pharmaceutical for Use with Wound Covering Materials

Zinc carbonate as a pharmaceutical product of the inorganic composition of the invention is free of a drying action or antimicrobial properties in contrast with zinc oxide and is useful as an additive to the active ingredient or other components of the pharmaceutical. Specifically, it can be used as an additive to a pharmaceutical composition as well as an additive to cosmetics and can exert different, synergistic, or enhanced effects on the substances to which the additives were added.

EXAMPLES

The inorganic composition of the invention will be described in detail using the examples below, but the invention is not limited thereto.

Preparation Example 1

500 mL of 0.08 M aqueous sodium hydrogen carbonate solution was prepared in a reaction vessel, and 1000 mL of a 0.1 M aqueous zinc nitrate solution was separately prepared as a drip reaction solution. 30 wt % aqueous sodium hydroxide solution was prepared as a pH adjusting solution.

Using a pH controller to which a pump was connected, the aqueous zinc nitrate solution and aqueous sodium hydroxide solution were added dropwise with the above-mentioned aqueous sodium hydrogen carbonate solution being maintained at pH 9.0 under stirring.

After all of the aqueous zinc nitrate solution was added, the reaction solution was stirred for 16 hours and was allowed to stand.

After that, the reaction solution was solid-liquid separated by centrifugation, and the obtained solid was washed with water; centrifugation was repeated three times. The washed precipitate was vacuum dried to obtain a hydrozincite having the composition range shown in Formula (1).

Preparation Example 2 pH at synthesis was set to 6.0 to 10, and various samples were prepared by the same process as in Preparation Example 1 while varying the pH at the time of preparation including that of Preparation Example 1 (pH 9.0). At pH of less than 6.5, since the pH was too low, the amount of precipitate recovered was significantly low.

Preparation Example 3

500 mL of 0.08 M aqueous sodium hydrogen carbonate solution was prepared in a reaction vessel, and 1000 mL of 0.1 M aqueous zinc sulfate solution was separately prepared as a drip reaction solution. 30 wt % aqueous sodium hydroxide solution was prepared as a pH adjusting solution.

Using a pH controller to which a pump was connected, the aqueous zinc sulfate solution and aqueous sodium hydroxide solution were added dropwise with the above-mentioned aqueous sodium hydrogen carbonate solution being maintained at pH 9.0 under stirring.

After all of the aqueous zinc sulfate solution was added, the reaction solution was stirred for 16 hours and was allowed to stand.

After that, the reaction solution was solid-liquid separated by centrifugation, and the obtained solid was washed with water; centrifugation was repeated three times. The washed precipitate was vacuum dried to obtain a hydrozincite having the composition range shown in Formula (2).

Preparation Example 4

500 mL of 0.08 M aqueous sodium hydrogen carbonate solution was prepared in a reaction vessel, and 1000 mL of a 0.1 M aqueous zinc chloride solution was separately prepared as a drip reaction solution. 30 wt % aqueous sodium hydroxide solution was prepared as a pH adjusting solution.

Using a pH controller to which a pump was connected, the aqueous zinc chloride solution and aqueous sodium hydroxide solution were added dropwise with the above-mentioned sodium hydrogen carbonate solution being maintained at pH 9.0 under stirring.

After all of the aqueous zinc chloride solution was added, the reaction solution was stirred for 16 hours and was allowed to stand.

After that, the reaction solution was solid-liquid separated by centrifugation, and the obtained solid was washed with water; centrifugation was repeated three times. The washed precipitate was vacuum dried to obtain a hydrozincite having the composition range shown in Formula (3).

(Dissolution Test)

Figure 8:
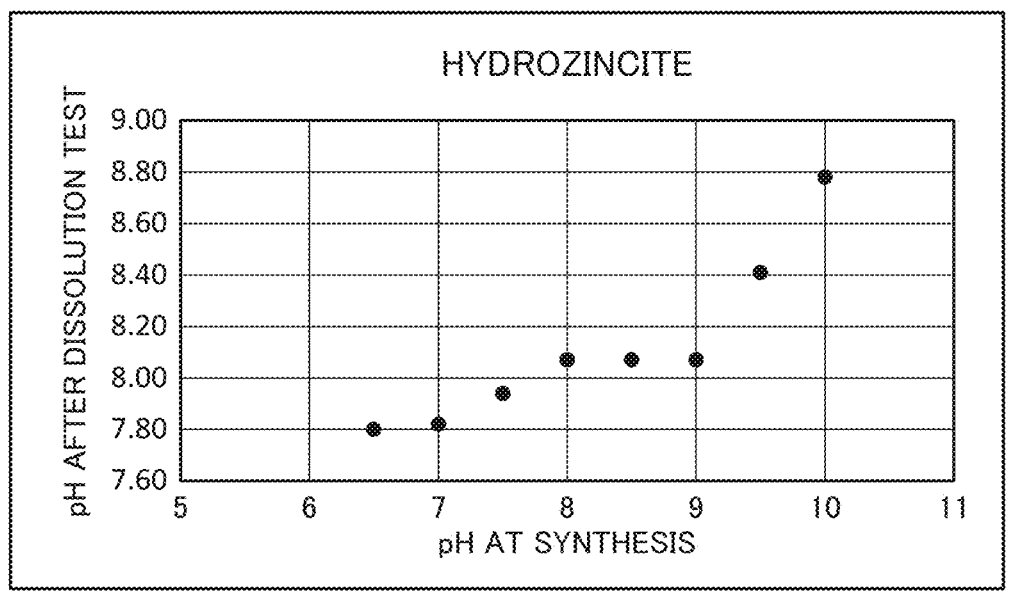
FIG. 8 is a graph showing the relationship between pH of hydrozincite at synthesis and pH after a dissolution test.
Figure 9:
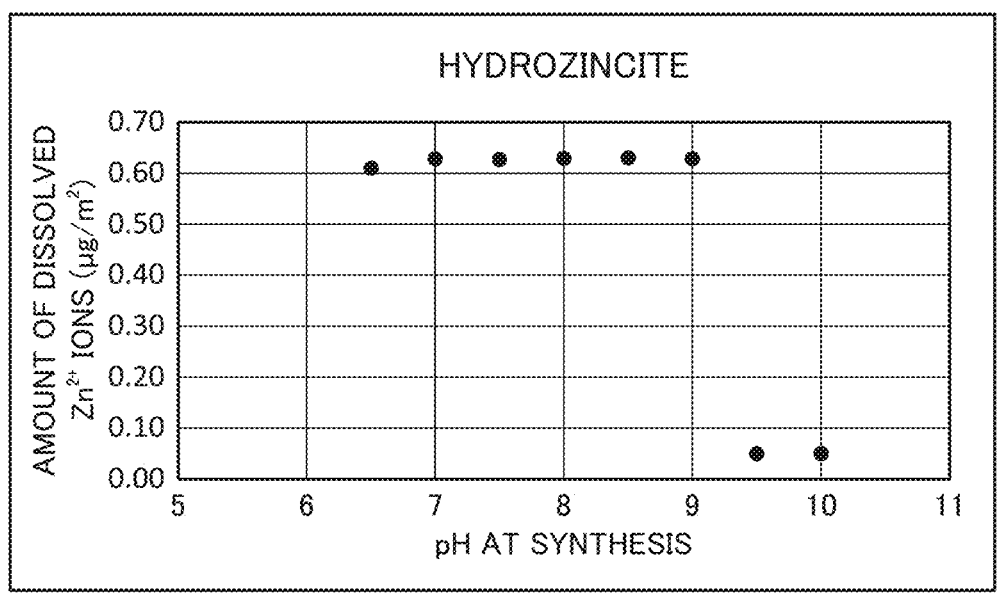
FIG. 9 is a graph showing the relationship between pH of hydrozincite at synthesis and the amount of dissolved $Zn^{2+}$ ions after the dissolution test.

A dissolution test using 30 g of saline for 0.6 g of each dry powder obtained in Preparation Example 2 was performed by stirring method, and the amount of dissolved $Zn^{2+}$ ions and pH were measured. In the method of the dissolution test, the BET specific surface area of the hydrozincite-containing zinc carbonate hydroxide hydrate was 10 to 150 $m^2/g$, the mass ratio of the hydrozincite-containing zinc carbonate hydroxide hydrate to the saline was 1:50, and the time for stirring using a rotor at 500 rpm was set to be 3 hours. The pH and $Zn^{2+}$ ion concentration after the dissolution test were measured. The results are shown in FIGS. 8 and 9, and Table 2.

Figure 10:
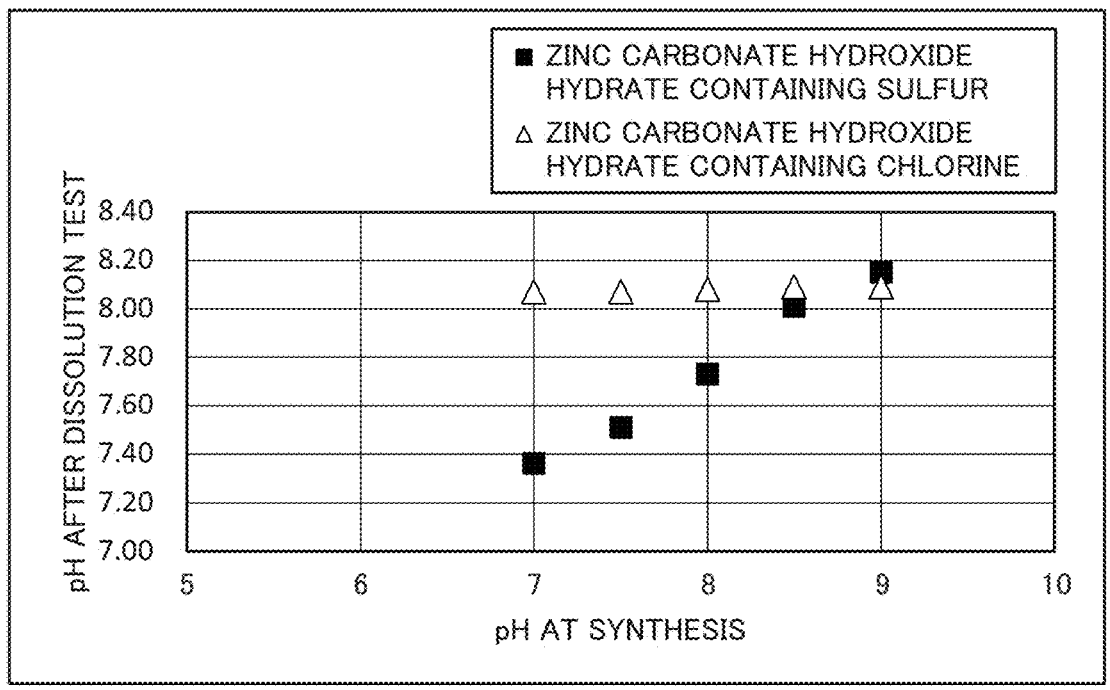
FIG. 10 is a graph showing the relationship between pH at synthesis of the zinc carbonate hydroxide hydrate containing sulfur and the zinc carbonate hydroxide hydrate containing chlorine, which are the inorganic compositions of the invention, and the pH after the dissolution test.
Figure 11:
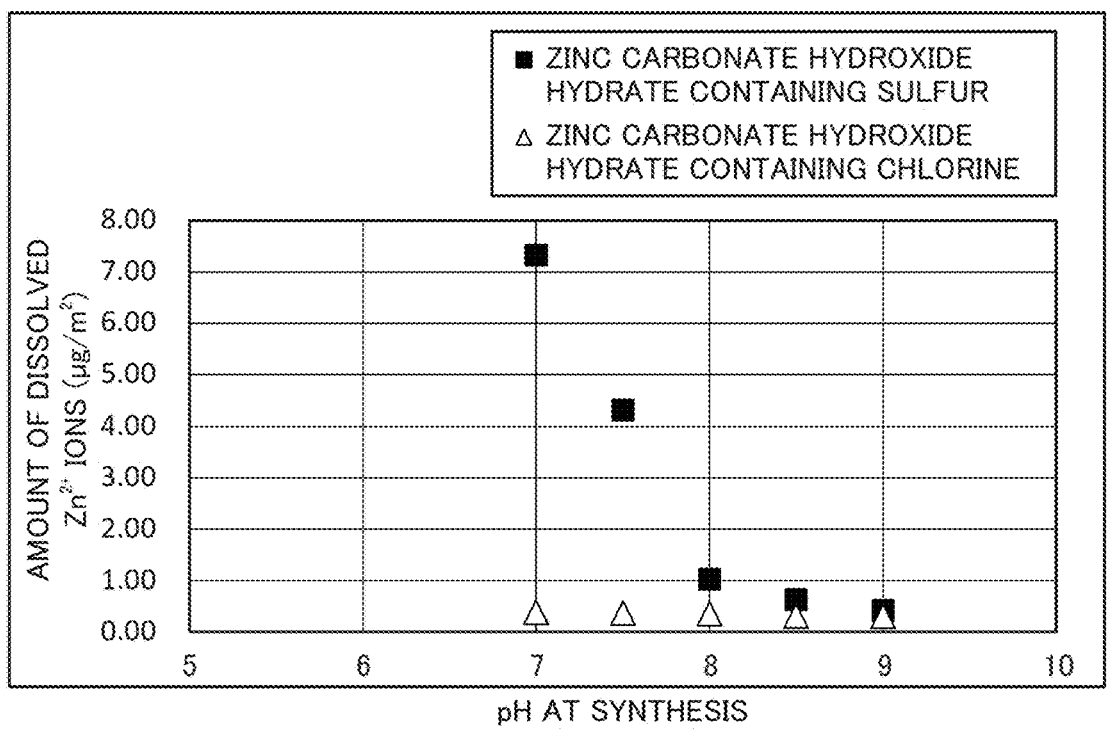
FIG. 11 is a graph showing the relationship between pH at synthesis of the zinc carbonate hydroxide hydrate containing sulfur and the zinc carbonate hydroxide hydrate containing chlorine, which are the inorganic compositions of the invention, and the amount of dissolved $Zn^{2+}$ ions after the dissolution test.

Additionally, the pH and $Zn^{2+}$ ion concentrations after the dissolution test obtained under the same conditions as described above for the zinc carbonate hydroxide hydrate containing not less than 0.1 mass % and less than 1.5 mass % of sulfur as S mainly as a result of substitution of carbonate ions with $SO_4^{2-}$ ions and the zinc carbonate hydroxide hydrate containing not less than 0.05 mass % and less than 1 mass % of chlorine as Cl mainly as a result of substitution of carbonate ions with $Cl^-$ ions were measured, and the results are shown in FIGS. 10, 11, and Tables 3 and 4.

TABLE 2

| | pH at synthesis | | | | | | | | |
|---|---|---|---|---|---|---|---|---|---|
| | 6 | 6.5 | 7 | 7.5 | 8 | 8.5 | 9 | 9.5 | 10 |
| pH after dissolution test | — | 7.80 | 7.8 | 7.94 | 8.07 | 8.07 | 8.07 | 8.41 | 8.78 |
| Amount of dissolved $Zn^{2+}$ ions after dissolution test ($\mu g/m^2$) | — | 0.61 | 0.63 | 0.63 | 0.63 | 0.63 | 0.63 | 0.05 | 0.05 |

TABLE 3

| pH at synthesis | 7 | 7.5 | 8 | 8.5 | 9 |
|---|---|---|---|---|---|
| pH after dissolution test. | 7.36 | 7.51 | 7.73 | 8.01 | 8.15 |
| Amount of dissolved $Zn^{2+}$ ions after dissolution test ($\mu g/m^2$) | 7.33 | 4.32 | 1.02 | 0.63 | 0.42 |

TABLE 4

| pH at synthesis | 7 | 7.5 | 8 | 8.5 | 9 |
|---|---|---|---|---|---|
| pH after dissolution test | 8.07 | 8.07 | 8.08 | 8.09 | 8.09 |
| Amount of dissolved $Zn^{2+}$ ions after dissolution test ($\mu g/m^2$) | 0.38 | 0.37 | 0.35 | 0.31 | 0.30 |

As a comparison, a dissolution test was performed using zinc oxide of reagent grade. The amount of dissolved $Zn^{2+}$ ions was sufficient; however, as zinc oxide has a drying effect as well as antimicrobial properties, it is strongly stimulative when used in the therapeutic agent for a skin wound or skin roughness. When the dissolution test was performed using zinc hydroxide, the dissolution amount was as significantly low as less than 0.1 $\mu g/m^2$.

Pharmaceutical Example 1

To an approximately 500 g SD rat, 0.2 mL/500 g of 2% Sederac (xylazine) was administered by intramuscular injection and the rat was sedated, and then, 2% of sevoflurane inhalation anesthetic was used to carry out a general anesthesia. Following local anesthesia by administering xylocaine (lidocaine+2% adrenaline) to the rat ventral side, a wound with all thickness skin loss of a diameter of 10 mm from epidermis reaching up to subcutaneous tissue was created, and 0.01 g of the powder of the above-mentioned Preparation Example 1 was applied to the created wound with all thickness skin loss (FIG. 2, left), and further covered with Duoactive which is a medical wound covering material (FIG. 2, right). The wound at the time of preparation is shown in FIG. 3A, and once covered with the wound covering material, the healing state after 2 weeks of feeding is shown in FIG. 3B. Examinations on the healing state of the wound site and the skin formation state using tissue staining were conducted.

The rate of re-epithelialization of the wound site was about 96% as measured by the method shown in FIGS. 3 and 4. On the other hand, the rate of re-epithelialization was about 78% when only covered with the medical wound covering material without using Preparation Example 1. Based on this, it can be said that the application of the therapeutic agent for a skin wound or skin roughness of the invention is extremely effective in wound healing.

Figure 5A:
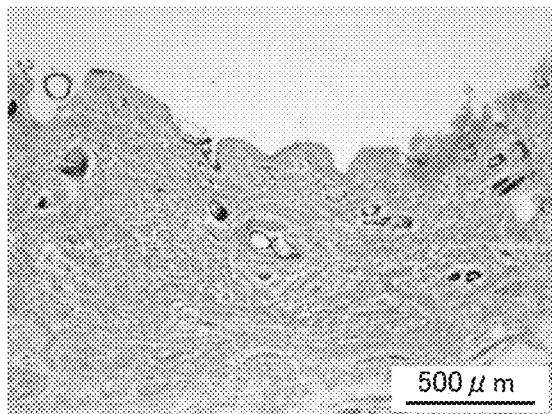
FIG. 5A is a micrograph of a cross section of stained skin after two-week treatment of the wound that was produced as described in Pharmaceutical Example 1 using Preparation Example 1.
Figure 5B:
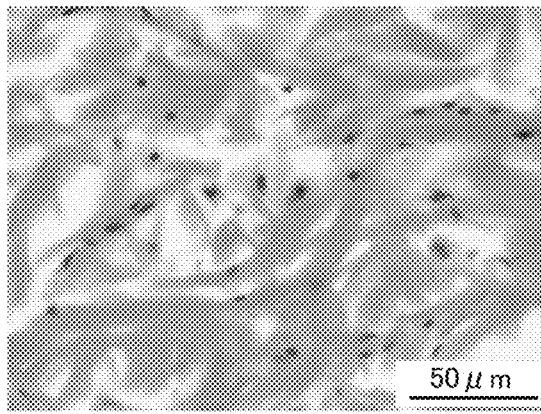
FIG. 5B is an enlarged view of FIG. 5A.

The regenerated skin tissue was excised from the rat and Hematoxylin-Eosin (H-E) staining was performed. Hair root sites and fibroblasts were observed in autologous skin (FIG. 6) and they were highly healthy. On the other hand, when the powder of Preparation Example 1 was applied, as shown in FIG. 5, hairballs (a stage before turning into a hair root) and robust fibroblasts were observed, and no polynuclear leukocytes or lymphocytes, which are inflammatory cells, were observed. In other words, it is believed that the treatment by the application of the therapeutic agent for a skin wound or skin roughness of the invention can not only regenerate skins without causing inflammation but also regenerate the hair root. Thus, the pharmaceuticals of the invention not only have a healing effect on the skin wound shown in the Preparation Examples but also on similar wounds caused by severe roughness.

Pharmaceutical Example 2

A wound with all thickness skin loss was created as in Pharmaceutical Example 1, and powder of each sample from Preparation Example 2 was applied to the created wound with all thickness skin loss and further covered with Duoactive which is a medical wound covering material. The re-epithelialization rate was between 80 and 90%, and the pharmaceutical agent of the invention, which was obtained at pH in a range of not less than 6.5 and less than 9.5 as a manufacturing condition, has an excellent healing effect.

Pharmaceutical Example 3

A wound with all thickness skin loss was created as in Pharmaceutical Example 1, and each powder of Preparation Examples 3 and 4 was applied to the created wound with all thickness skin loss and further covered with Duoactive which is a medical wound covering material. The re-epithelialization rate was between 80 and 90%, and the pharmaceutical of the invention, which was obtained at pH in a range of not less than 6.5 and less than 9.5 as a manufacturing condition, has an excellent healing effect.

Pharmaceutical Example 4

A formulation was obtained by mixing hydrozincite having a composition range shown in Formula (1) obtained in Preparation Example 1 and zinc oxide obtained by calcinating the hydrozincite at a calcination temperature of 1200° C.

(Measurement Method of Re-Epithelialization Rate)

As shown in FIG. 3, magnified photographs of skin were taken at the time of wound creation (FIG. 3A) and after treatment (FIG. 3B). The initial wound site at the time of wound creation was measured and drawn in the post-treatment photograph with a solid line. The area of the initial wound site $W_0$ shown in FIG. 4 was measured, the area of the unhealed site ($W_t$) after treatment was determined by Image J [open source published on the web; Wayne Rasband (NIH)], and the rate of re-epithelialization is calculated from the measured area using the following equation. The re-epithelialization rate in the measurement of Pharmaceutical Example 1 shown in FIG. 3 and FIG. 4 was 95.8%.

Re-epithelialization rate (%)=$(W_0-W_t)/W_0 \times 100\%$ (Tissue Staining and Hematoxylin-Eosin (H-E) Staining)

The method of tissue staining was carried out as follows: wound site trimming (excision)→formalin fixation→degreasing treatment (immersed in xylene for 24 hours)→dehydration treatment.

The dehydration treatment was carried out as follows: samples were immersed in 70% ethanol for 12 hours and the ethanol was removed by volatilization, and then the samples were dehydrated by 80% ethanol, 90% ethanol, and 95.5% ethanol for 30 minutes each, and washed twice with xylene.

The samples were then embedded in paraffin→sections were prepared→H-E staining was carried out. The cell nucleus was stained with hematoxylin in a blue-violet color and the cytoplasm, collagen fibers, and muscle fibers were stained in red color with eosin.→The sample after staining was enclosed in a prepared slide, and the microscopical observation results of Pharmaceutical Example 1 are shown in FIG. 5.

Figure 6A:
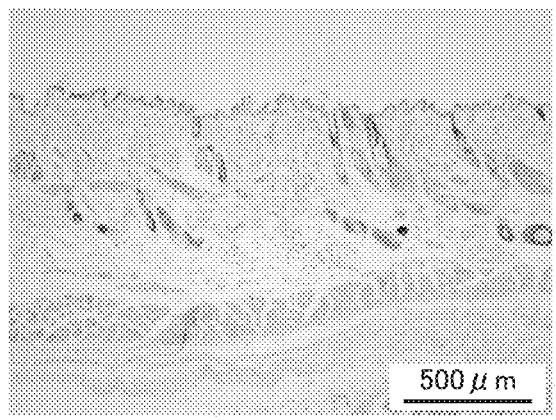
FIGS. 6A and 6B are photographs of normal skin taken at the same magnification and the same timing as in FIG. 5, serving as the control against FIG. 5.
Figure 6B:
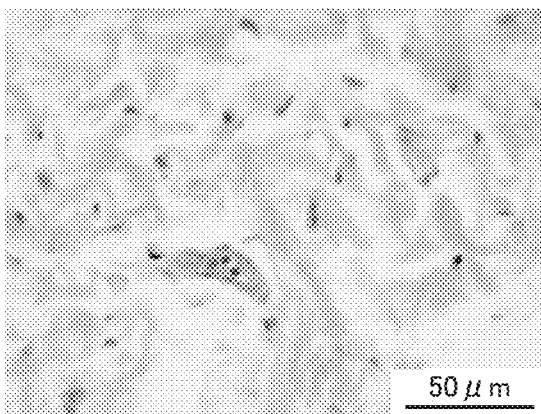

Observation results from similarly treated and similarly stained normal skin for comparison are shown in FIG. 6.

Table 5 below shows pH after the dissolution test and the results of evaluation on wound healing effects after 2 weeks (re-epithelialization rate, collagen regeneration, hairball regeneration, and granulation formation) obtained from Pharmaceutical Example 2. The control did not use a pharmaceutical example and it was only covered with Duoactive which is a medical wound covering material.

TABLE 5

| | pH at synthesis | | | | | | | | | |
|---|---|---|---|---|---|---|---|---|---|---|
| | 6 | 6.5 | 7 | 7.5 | 8 | 8.5 | 9 | 9.5 | 10 | — |
| pH after dissolution test | — | 7.80 | 7.82 | 7.94 | 8.07 | 8.07 | 8.07 | 8.41 | 8.78 | — |
| Amount of dissolved $Zn^{2+}$ ions after dissolution test ($\mu m^2$) | — | 0.61 | 0.63 | 0.63 | 0.63 | 0.63 | 0.63 | 0.05 | 0.05 | — |

TABLE 5-continued

Healing state after 2 weeks

|  |  |  |  |  |  |  |  |  |  | Control |
|---|---|---|---|---|---|---|---|---|---|---|
| Degree of re-epithelialization | — | 1.1 | 1.1 | 1.6 | 1.4 | 1.3 | 1.4 | — | — | 1 |
| Collagen thickness | — | ○ | ○ | ○ | ○ | ○ | ○ | — | — | Δ |
| Collagen Orientation | — | ○ | ○ | ○ | ○ | ○ | ○ | — | — | X |
| Hairballs | — | ○ | ○ | Δ | Δ | Δ | X | — | — | X |
| Granulation formation | — | ○ | ○ | ○ | ○ | ○ | ○ | — | — | ○ |

Table 6 and Table 7 below show the pH after the dissolution test and the results of evaluation on wound healing effects after 2 weeks (re-epithelialization rate, collagen regeneration, hairball regeneration, and granulation formation) obtained from each of Pharmaceutical Examples 3 and 4.

TABLE 6

| | pH at synthesis | | | | | |
|---|---|---|---|---|---|---|
| | 7 | 7.5 | 8 | 8.5 | 9 | — |
| pH after dissolution test | 7.36 | 7.51 | 7.73 | 8.01 | 8.15 | — |
| Amount of dissolved $Zn^{2+}$ ions after dissolution test ($\mu g/m^2$) | 7.33 | 4.32 | 1.02 | 0.63 | 0.42 | — |

Healing state after 2 weeks

| | | | | | | Control |
|---|---|---|---|---|---|---|
| Degree of re-epithelialization | 1.1 | 1.08 | 1.05 | 1 | 0.95 | 1 |
| Collagen thickness | ○ | ○ | ○ | ○ | Δ | Δ |
| Collagen Orientation | ○ | ○ | Δ | Δ | Δ | X |
| Hairballs | Δ | Δ | Δ | X | X | X |
| Granulation formation | ○ | ○ | ○ | ○ | Δ | ○ |

TABLE 7

| | pH at synthesis | | | | | |
|---|---|---|---|---|---|---|
| | 7 | 7.5 | 8 | 8.5 | 9 | — |
| pH after dissolution test | 8.07 | 8.07 | 8.08 | 8.09 | 8.09 | — |
| Amount of dissolved $Zn^{2+}$ ions after dissolution test ($\mu g/m^2$) | 0.38 | 0.37 | 0.35 | 0.31 | 0.30 | — |

Healing state after 2 weeks

| | | | | | | Control |
|---|---|---|---|---|---|---|
| Degree of re-epithelialization | 1.05 | 1.05 | 1.02 | 1.02 | 1.01 | 1 |
| Collagen thickness | ○ | ○ | ○ | ○ | ○ | Δ |
| Collagen Orientation | ○ | ○ | ○ | ○ | Δ | X |
| Hairballs | Δ | Δ | X | X | X | X |
| Granulation formation | ○ | ○ | ○ | ○ | ○ | ○ |

The results, in which that of the control as a comparison is included, are also shown in Tables 5 to 7. Hydrozincite which is the product of the invention is recognized to be clearly effective in the regenerated tissue, particularly, in the appearance of collagens.

Accordingly, it is believed that the product of the invention may be applied to a commercially-available organic based wound covering material, whereby the use of the inorganic based material of the therapeutic agent of the invention leads to hybridization of organic based/inorganic based, materials, resulting in a great synergistic effect and a great improvement in the would healing capability.

The evaluation method of Tables 5 to 7 is based on evaluation according to the above-described measurement method where the re-epithelialization rate of the control is regarded as 1. For the evaluation of collagen, thick collagen fibers extending in one direction were observed. With respect to hairballs, the observation results show whether the hairballs could be confirmed. For the evaluation of granulation formation, it was determined whether tissues composed of capillary vessels and fibroblasts were observed.

Collagen: For evaluation of collagen, collagen fiber thickness and orientation were assessed in comparison with healthy skin cells.

Collagen thickness: x: Very thin
Δ: Thin
○: Slightly inferior
◉: Same as healthy skin cells
Collagen Orientation: x: Random
Δ: Very inferior
○: Slightly inferior
◉: Same as healthy skin cells
Hairballs: x: No formation of hairballs is observed.
Δ: Slight formation of hairballs is observed.
○: Hairballs are formed.
◉: The formation of hairballs is prominently observed.
Granulation formation: x: No granulation is observed.
Δ: Granulation is slightly observed.
○: Granulation is observed.
◉: Granulation is prominently observed.

(Application Form)

The pharmaceutical examples described above take an application form of powder for use in treatment techniques in which the basic zinc salt powder of the invention is spread onto the wound part and Duoactive which is a medical wound covering material covers the wound part. The inventors conducted diligent research on the application form (treatment technique) of the basic zinc salt powder of the invention. The application form (treatment technique) and the healing effect when used as an ointment along with a covering material will be described hereinafter.

Preparation Example 5

Zinc sulfate was used as a zinc raw material as in Preparation Example 3, and pH for the precipitate generation reaction was changed. 500 mL of 0.08 M aqueous sodium hydrogen carbonate solution was prepared in a reaction vessel, and 1000 mL of 0.1 M aqueous zinc sulfate solution was separately prepared as a drip reaction solution. 30 wt % aqueous sodium hydroxide solution was prepared as a pH adjusting solution.

Using a pH controller to which a pump was connected, the aqueous zinc sulfate solution and aqueous sodium hydroxide solution were added dropwise with the above-mentioned sodium hydrogen carbonate solution being maintained at pH 7.0 under stirring.

After all of the aqueous zinc sulfate solution was added, the reaction solution was stirred for 16 hours and was allowed to stand.

After that, the reaction solution was solid-liquid separated by centrifugation, and the obtained solid was washed with water; the centrifugation was repeated three times. The washed precipitate was vacuum dried to obtain a hydrozincite having the composition range shown in Formula (2). Ointments and covering materials were prepared using this dry powder.

Ointment Preparation Example 1

4.9 g of white vaseline was placed, in a 50-mL beaker, heated to 60° C., and 0.1 g of liquid paraffin was added and mixed, after 5 g of dry powder obtained in Preparation Example 5 was added thereto and sufficiently stirred to produce 10 g of ointment (amount of active ingredient: 50 mass %). The ointment was applied to the created wound with all thickness skin loss, and observation of wound appearance after 2 weeks and tissue observation of the wound part were carried out. Results are shown in Table 8.

Comparative Example 1, Using Only an Ointment Base as a Control

Only the ointment base made of white vaseline and paraffin which does not contain the active ingredient was applied as a comparative example to the wound with all thickness skin loss created as in the above-mentioned Ointment Preparation Example, and observation of wound appearance after 2 weeks and tissue observation of the wound part were carried out as a control including the base only. Results are shown in Table 8.

Covering Material Usage Examples 2 and 3

Using the powder obtained in Preparation Example 5, in Covering material usage example 2, 5 g of the dry powder of Preparation Example 1 was kneaded into 5 g of hydrogel (active ingredient: 50 mass %), and in Covering material usage example 3, the powder of Preparation Example 1 was fixed onto a hydrogel surface (wound contacting side) by a shot blasting method in an amount of 40 mass % (4 g of dry powder for 6 g of hydrogel), whereby Covering material usage example 2 and Covering material usage example 3 were prepared, respectively. Here, the hydrogels used are those used in the commercially available medical wound covering material Duoactive. Covering material usage example 2 and Covering material usage example 3 were each applied to the wound with all thickness skin loss as created in the above-mentioned Ointment Preparation Example, and observation of wound appearance after 2 weeks and tissue observation of the wound part were carried out. Results are shown in Table 8.

Comparative Example 2, Using Only the Covering Material as a Control

A control (comparative example) in which the created wound with all thickness skin loss was merely covered with Duoactive was prepared, and observation of wound appearance after 2 weeks and tissue observation of the wound part were carried out. Results are shown in Table 8.

The Ointment Preparation Example 1, and Covering material usage examples 2 and 3 were all evaluated for healing effect after 2 weeks (collagen thickness, collagen orientation, hairball regeneration, and granulation formation) and the results are shown. The criteria are the same as in Tables 5 to 7.

TABLE 8

|  | Ointment Preparation Example 1 | Control only using base | Covering material usage example 2 | Covering material usage example 3 | Control only using covering material |
|---|---|---|---|---|---|
| Collagen thickness | ⊚ | Δ | ⊚ | ⊚ | Δ |
| Collagen Orientation | ⊚ | X | ⊚ | ⊚ | X |
| Hairballs | ⊚ | X | ⊚ | ⊚ | X |
| Granulation formation | ⊚ | Δ | ⊚ | ⊚ | ○ |

The hydrozincite which can be utilized as a pharmaceutical or medical device of the invention in Ointment Preparation Example 1 and Covering material usage examples 2 and 3 achieves recovery of the regenerated tissues to the same level as of a normal skin tissue, in particular, in terms of the appearance of collagen, and thus exhibits great effect, which is equivalent to the case of the powder application in Pharmaceutical Example 1 and Pharmaceutical Example 2. The hydrozincite is also highly effective from the perspective of convenience at the clinical site.

INDUSTRIAL APPLICABILITY

The inorganic composition having excellent zinc ion sustained-release properties of the invention allows an appropriate sustained-release of the zinc ions at a suitable condition when used as a pharmaceutical, and it can be used as an active ingredient for pharmaceuticals. The inorganic composition of the invention has an excellent stability, and the manufacturing method thereof is simple; therefore, the inorganic composition is industrially useful.

REFERENCE SIGNS LIST

1 Skin wound or skin roughness which reaches up to dermis via epidermis, or pressure ulcers which reaches up to peritoneum via epidermis and dermis.

Specific Embodiments

The invention includes the following specific embodiments.

[Claim 1]

The invention claimed is:

1. An inorganic composition, which can be used as an active ingredient of a pharmaceutical, comprising hydrozincite-containing zinc carbonate hydroxide hydrate, wherein the hydrozincite-containing zinc carbonate hydroxide hydrate is produced by drying a precipitate, wherein the precipitate is obtained by adding aqueous zinc nitrate solution, aqueous zinc sulfate solution or aqueous zinc chloride solution and aqueous sodium hydroxide solution dropwise to aqueous sodium hydrogen carbonate solution, a pH of the aqueous sodium hydrogen carbonate solution being maintained within a range of 6.5 to 9 by means of a pH controller, wherein the hydrozincite-containing zinc carbonate hydroxide hydrate has an amount of dissolved $Zn^{2+}$ ions of not less than 0.1 µg/m² but not more than 7.33 µg/m² and pH of not less than 7.2 and less than 8.3 after a dissolution test using stirring method;

wherein, in the dissolution test, a BET specific surface area of the hydrozincite-containing zinc carbonate hydroxide hydrate is from 10 to 150 m²/g, a mass ratio of the hydrozincite-containing zinc carbonate hydroxide hydrate to the saline is 1:50, and a time for stirring at 37° C. using a rotor at 500 rpm is 3 hours.

2. The inorganic composition according to claim 1, wherein the hydrozincite-containing zinc carbonate hydroxide hydrate is represented by Formula (1) below, and the molar ratio of Zn to to $CO_3$ is $Zn/CO_3$=2.5-3.3;

$$Zn_{4-6}(CO_3)_{1-3}(OH)_{5-6} \cdot nH_2O \quad (1)$$

where n is 0 to 6.

3. The inorganic composition according to claim 1, wherein the hydrozincite-containing zinc carbonate hydroxide hydrate is represented by Formula (2) below, and the molar ratio of Zn Formula (2) below, and the molar ratio of Zn to $((1-x)CO_3+x(SO_4))$ is $Zn/((1-x)CO_3+x(SO_4))$=2.5-3.3;

$$Zn_{4-6}((1-x)CO_3+x(SO_4))_{1-3}(OH)_{5-6} \cdot nH_2O \quad (2)$$

where n is 0 to 6, And X is 0.005 to 0.1.

4. The inorganic composition according to claim 1, wherein the hydrozincite-containing zinc carbonate hydroxide hydrate is represented by Formula (3), and the molar ratio of Zn to $((1-x)CO_{3+x}$ is $Zn/((1-x)CO_{3+x}Cl)$ is $Zn/((1-x)CO_3+xCl)$=2.5-3.3;

$$Zn_{4-6}((1-x)CO_{3+xCl})_{1-3}(OH)_{5-6} \cdot nH_2O \quad (3)$$

where n is 0 to 6, And x is 0.005 to 0.1.

5. The inorganic composition according to claim 2, wherein, in an XRD diffraction pattern of the hydrozincite-containing zinc carbonate hydroxide hydrate represented by the chemical formula of the Formula (1), a structure of $Zn_5(CO_3)_2(OH)_6 \cdot nH_2O$ (x is 0.005-0.1 and n is 0-6) is dominant; where, a axis is 13.3 to 13.8, b axis is 6.2 to 6.4, c axis is 5.25 to 5.5, and β is 94.9 to 97.5.

6. The inorganic composition according to claim 2, wherein the pharmaceutical is a therapeutic agent for a skin wound or skin roughness, and when the therapeutic agent is dissolved in saline and used, a ratio of the pharmaceutical to saline is from 0.1 g/L to 100 g/L, and the inorganic composition is represented by the formula of the Formula (1), and when n=0 (anhydrous), the zinc concentration relative to a total amount of the pharmaceutical is from 45 mass% to 75 mass% as metal zinc, and the zinc concentration in the saline of the pharmaceutical is from 0.045 g/L to 75 g/L.

7. The inorganic composition according to claim 1, wherein the pharmaceutical is a therapeutic agent for a skin wound or skin roughness which reaches up to the dermis via the epidermis, or for pressure ulcers which reaches up to peritoneum via epidermis and dermis.

8. The inorganic composition according to claim 7, wherein the pharmaceutical is a medical device comprising a wound covering material retaining the therapeutic agent and the skin wound or skin roughness in a closed environment.

9. The inorganic composition according to claim 8, wherein the therapeutic agent for a skin wound or skin roughness is present by being applied to, contained in, or adhered to the wound covering material.

10. A method of manufacturing the inorganic composition according to claim 1, wherein the hydrozincite-containing zinc carbonate hydroxide hydrate is produced by drying a precipitate, and wherein the precipitate is obtained by adding aqueous zinc nitrate solution, aqueous zinc sulfate solution or aqueous zinc chloride solution and aqueous sodium hydroxide solution dropwise to aqueous sodium hydrogen carbonate solution, a pH of the aqueous sodium hydrogen carbonate solution being maintained within a range of 6.5 to 9 by means of a pH controller.

11. The inorganic composition according to claim 3, wherein in an XRD diffraction pattern of the hydrozincite-containing zinc carbonate hydroxide hydrate represented by the chemical formula of the Formula (2), a structure of $Zn_5((1-x) CO_3+xSO_4)_2(OH)_6 \cdot nH_2O$ (x is 0.005-0.1 and n is 0-6) is dominant; where, a axis is 13.3 to 13.8, b axis is 6.2 to 6.4, c axis is 5.25 to 5.5, and β is 94.9 to 97.5.

12. The inorganic composition according to claim 4, wherein in an XRD diffraction pattern of the hydrozincite-containing zinc carbonate hydroxide hydrate represented by the chemical formula of the Formula (3), a structure of $Zn_5((1-x) CO_3+xCl)_2(OH)_6 \cdot nH_2O$ (x is 0.005-0.1 and n is 0-6) is dominant; where, a axis is 13.3 to 13.8, b axis is 6.2 to 6.4, c axis is 5.25 to 5.5, and β is 94.9 to 97.5.

13. The inorganic composition according to claim 3, wherein the pharmaceutical is a therapeutic agent for a skin wound or skin roughness, and when the therapeutic agent is dissolved in saline and used, a ratio of the pharmaceutical to saline is from 0.1 g/L to 100 g/L, and the inorganic composition is represented by the formula of the Formula (2), and when n=0 (anhydrous), the zinc concentration relative to a total amount of the pharmaceutical is from 45 mass% to 75 mass% as metal zinc, and the zinc concentration in the saline of the pharmaceutical is from 0.045 g/L to 75 g/L.

14. The inorganic composition according to claim 4, wherein the pharmaceutical is a therapeutic agent for a skin wound or skin roughness, and when the therapeutic agent is dissolved in saline and used, a ratio of the pharmaceutical to saline is from 0.1 g/L to 100 g/L, and the inorganic composition is represented by the formula of the Formula (3), and when n=0 (anhydrous), the zinc concentration relative to a total amount of the pharmaceutical is from 45 mass% to 75 mass% as metal zinc, and the zinc concentration in the saline of the pharmaceutical is from 0.045 g/L to 75 g/L.

* * * * *